United States Patent

Chikama

[11] 4,024,858
[45] May 24, 1977

[54] ENDOSCOPE

[75] Inventor: Toshio Chikama, Tokyo, Japan

[73] Assignee: Machida Endoscope Co., Ltd., Tokyo, Japan

[22] Filed: Jan. 30, 1975

[21] Appl. No.: 545,587

[52] U.S. Cl. .................................................. 128/4
[51] Int. Cl.² ......................................... A61B 1/26
[58] Field of Search .................................. 128/4–8, 128/35 R, 351

[56] References Cited

UNITED STATES PATENTS

| 2,243,992 | 6/1941 | Wappler | 128/8 |
| 3,739,770 | 6/1973 | Mori | 128/6 |
| 3,788,304 | 1/1974 | Takahashi | 128/6 |

FOREIGN PATENTS OR APPLICATIONS

| 1,347,596 | 11/1963 | France | 128/4 |

Primary Examiner—Robert W. Michell
Assistant Examiner—Henry S. Layton
Attorney, Agent, or Firm—Peter L. Berger

[57] ABSTRACT

A flat tubular structure, which comprises two tubes arranged side by side and enclosed within an outer tube, with each of the inner tubes having a structure capable of bending but incapable of transmitting a twisting effort through the whole length when a torque is applied at one end, behaves such that when it is twisted at its one end, while holding its intermediate portion, its other end is twisted by the same amount, with its intermediate portion remaining flat without being twisted.

Such a flat tubular structure is used as a flexible tube portion of an endoscope. When the intermediate portion of such a flexible tube portion is located within the gullet, by turning a grip portion outside the body the tip portion within the body is turned by the same amount, as the grip portion and the intermediate portion is prevented from turning since it bears against the gullet. With this construction, it is possible to observe the inside of the body at various angles without squeezing the windpipe, that is, with less pain to the patient. Also, an endoscope having a flexible tube portion of an increased sectional area can be produced.

8 Claims, 9 Drawing Figures

ENDOSCOPE

BACKGROUND OF THE INVENTION

Recently, the techniques concerning the construction and operation of endoscopes are quickly advancing, and now the endoscope is not a mere tool for observing the inside of the body but is also used as means for the treatment and extraction of poleave. As a consequence, the number of requisite items accommodated in the tube such as the pincette guide, water duct and air duct and also the diameter of the tube are increasing. Increasing the diameter of the tube, however, means increased pain for the patient; particularly, with a tube greater in diameter than the size of the gullet, various inconveniences are encountered due to pressure exerted to the windpipe.

As another aspect, for varying the orientation of the endoscope inserted inside the body, which will be required for varying the direction of transmitted light flux and image light flux through the light transmitting fiber bundle or varying the direction of flow of water, the tube tip is rotated by rotating the grip. Accordingly, the tube desirably has a circular sectional profile. However, the sectional profile of the gullet is normally rather flat, and which is not conformed to by the tube.

OBJECTS

An object of the invention is to increase the effective sectional area of the endoscope tube by making it flat and conforming it to the sectional shape of the gullet.

Another object of the invention is to provide an endoscope, which has a flat flexible tube portion constituted by two tubes arranged side by side and united at the opposite ends, at least one of said tubes being flexible but incapable of transmitting a twisting motion through the whole length, said flexible tube portion behaving such that by twisting its end connected to a grip, while holding its intermediate portion, its tip is twisted by the same amount as its grip end with its intermediate portion remaining flat without being twisted. In this manner the inside of the body can be observed without giving pain to the gullet despite the large sectional area of the flexible tube portion.

A further object of the invention is to provide an endoscope having a flexible tube portion, whose sectional area remains unchanged when it is twisted, thus eliminating undesired compressive or tensile effects upon the items accommodated within it at the time of its twisting.

SUMMARY

The invention features an endoscope having a flexible tube portion including two tubes in a set, said tubes having a braided structure or a structure constituted by three helically wound strips arranged one over another, an intermediate one of said helical strip being wound oppositely with respect to the other helical strips.

DETAILED DESCRIPTION OF THE INVENTION

Figure 1:
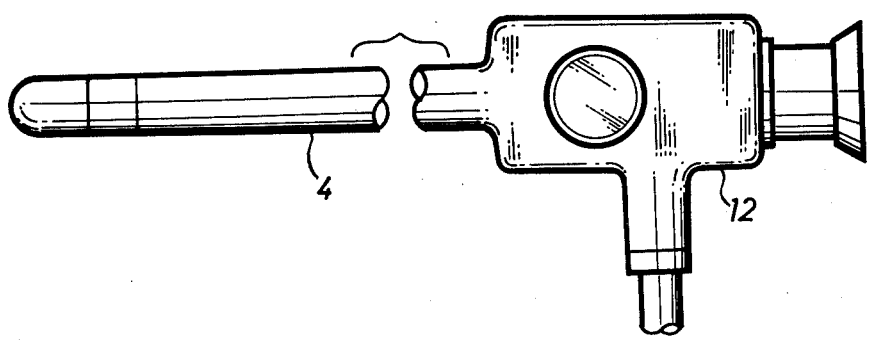
FIG. 1 is a side view, partly broken away, showing an endoscope.
Figure 2:
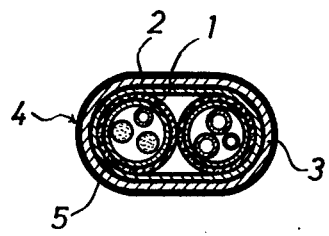
FIG. 2 is a section taken along line I—I.
Figure 3:
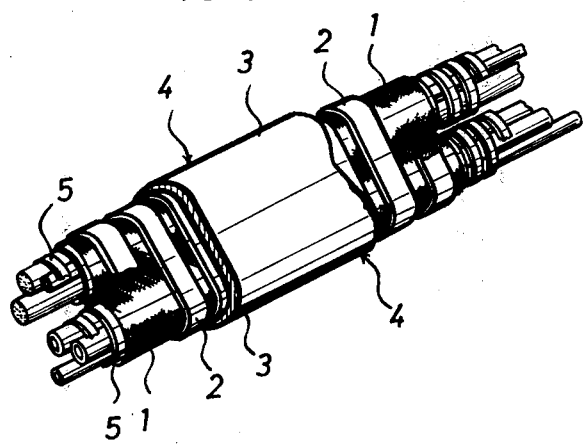
FIG. 3 is a fragmentary perspective view showing the construction of a flexible tube portion.

The endoscope according to the invention has a flexible tube portion 4, which comprises two inner tubes 1 of such material as a metal or a synthetic resin, these inner tubes having, for instance, a braided structure and being arranged side by side and secured to each other at the opposite ends, and an outer tube 3 covering the inner tubes via a helical strip 2 helically wound on the side-by-side arrangement of the two inner tubes. If it is necessary, each inner tube 1 may be provided with a helical metal strip 5 in close contact with its inner side.

Light transmission fiber bundles, pincette guides, air ducts, water ducts and other necessary parts are inserted in each of the two inner tubes.

Figure 6:
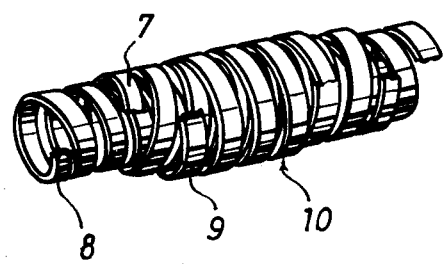
FIG. 6 is a fragmentary perspective view of part of another example of the flexible tube portion.
Figure 5:
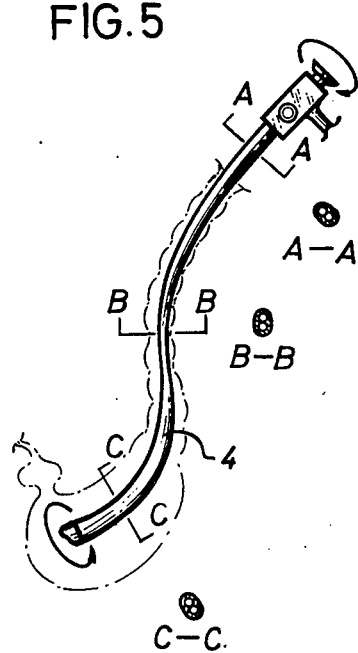
FIG. 5 is a schematic view of the endoscope in use.
Figure 7:
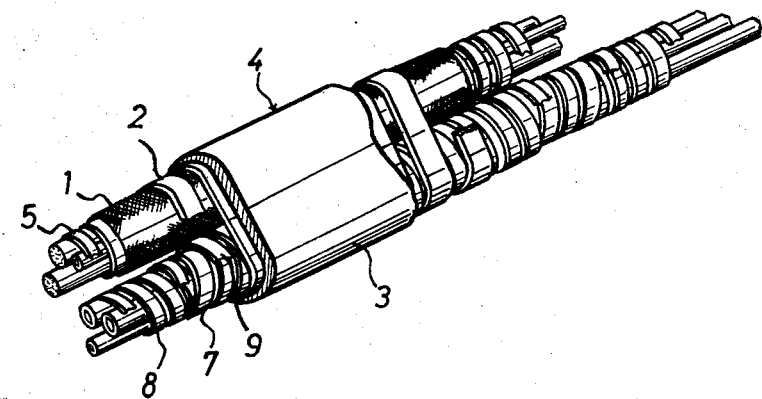
FIGS. 7, 8 and 9 are fragmentary perspective views showing part of further examples of the flexible tube portion.
Figure 8:
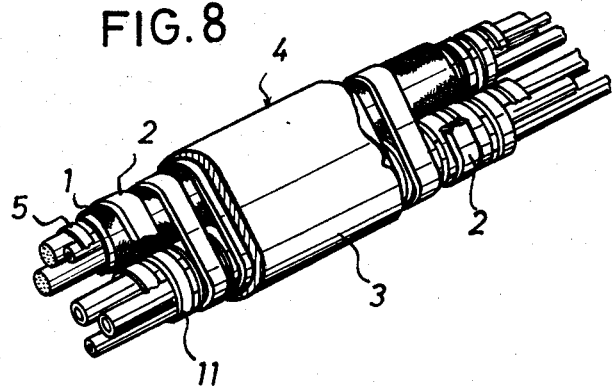
Figure 9:
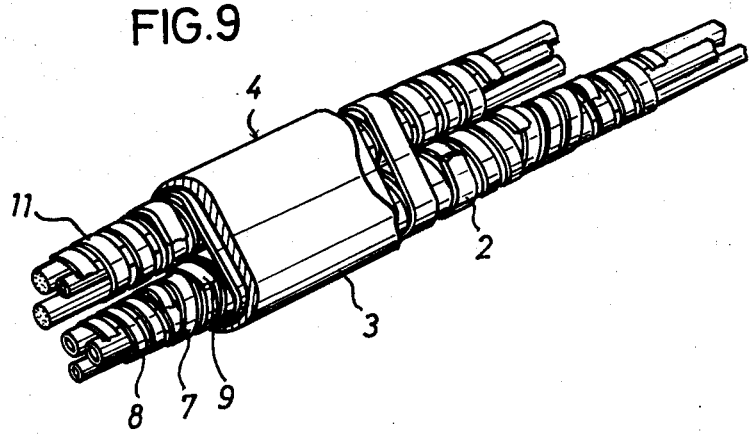

In another example of the flexible tube portion, each of the two inner tubes, shown in FIG. 6 and generally indicated at 10, has a structure consisting of three helically wound strips 7, 8 and 9, with the intermediate helical strip 7 wound oppositely with respect to the other two helical strips. In a further example of the flexible tube portion 4, shown in FIG. 7, one of the two inner tubes, namely tube 1, has the aforementioned braided structure, while the other inner tube 10 has the structure consisting of three helical strips. In still further examples of the flexible tube portion 4, shown in FIGS. 8 and 9, one of the inner tubes has the braided structure or structure formed by three helical strips, while the other inner tube 11 has a structure formed by a single helical strip.

In general, in the flexible tube portion at least one of the inner tubes is flexible but is incapable of twisting.

Figure 4:
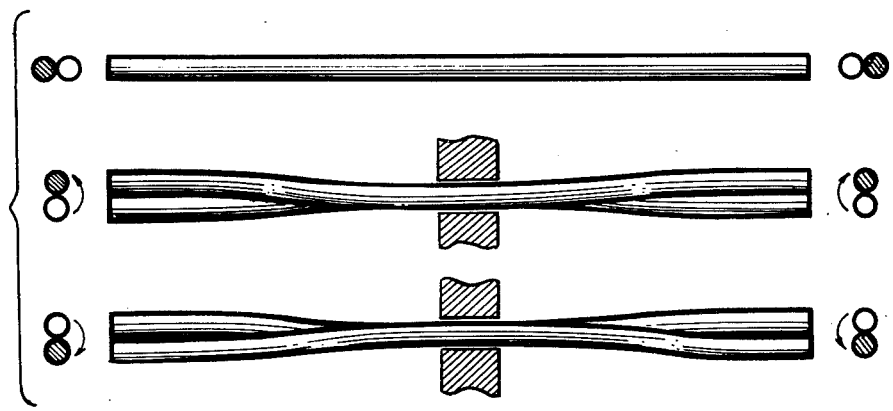
FIG. 4 illustrates the behavior of the flexible tube portion when it is twisted.

With such a construction of the flat flexible tube portion 4, by turning its one end (i.e. grip portion) while holding its intermediate portion against the gullet to which shape the intermediate portion conforms, its other end (i.e., its tip side) will be rotated in the same direction by the same amount of angle, with the intermediate held portion prevented from rotating by the gullet and retaining the flat state without being twisted as shown in FIG. 4.

To use the endoscope according to the invention for examining, for instance the stomach, it is inserted through the mouth into the body. At this time, an intermediate portion of the flexible tube portion 4 is located in the gullet and serves the role of the aforesaid held portion. Thus, the orientation of the endoscope tip located within the stomach can be changed by turning the grip at the other end, without the windpipe being squeezed for the section of the flexible tube portion located within the gullet is not twisted at all but remains flat. In this way, the angle of the endoscope tip can be freely varied without giving any pain to the patient.

As has been shown, since the flexible tube portion of the endoscope according to the invention has a flat shape conforming to the shape of the gullet, the sectional area of the flexible tube portion may be made substantially the same as that of the gullet. Thus, the effective area of the flexible tube portion can be increased, and hence a great number of items required for a greater number of treatment means and treatment purposes can be accommodated in the flexible tube portion. Nevertheless, since the flexible tube portion is constituted by two inner tubes, at least one of which is flexible but incapable of twisting, by changing the angle of its tip its intermediate section located within the gullet remains flat and does not tend to squeeze or otherwise press the windpipe via the gullet, thus giving less pain to the patient.

Further, since the sectional profile provides for increased effective sectional area, it can be easily inserted (or swallowed) compared to an endoscope having a cylindrical flexible tube portion of the same sectional area.

Furthermore, since at least one of the inner tubes of the flexible tube portion is flexible but is incapable of twisting, the sectional area of each inner tube will not be varied even when the flexible tube portion is twisted, so that undesired compressive or tensile effects on the items within the tube are eliminated.

What is claimed is:

1. An endoscope for insertion into the body through the mouth and into the gullet comprising a grip portion end located outside the body, an intermediate portion for location in the gullet, and a tip end, said intermediate portion being flexible and comprising two tubes arranged side by side, said two tubes being joined at said tip and grip portion ends, said intermediate portion including said two tubes comprising a fixed cross-sectional non-circular shape having opposite sides thereof in parallel relation to conform to the shape of the gullet, said intermediate portion retaining said non-circular shape and bearing against the gullet to prevent rotation of the intermediate portion held in the gullet while transmitting angular rotation of the grip portion end to the tip end so that said tip and grip portion ends rotate an equal amount.

2. An endoscope according to claim 1, wherein said non-circular shape comprises said opposite parallel sides joined at their ends by circular segments.

3. An endoscope according to claim 1, wherein each of said tubes is formed as a braided structure.

4. An endoscope according to claim 1, wherein each of said tubes comprises: three helically wound strips arranged one over another, with an intermediate one of said helical strips being wound oppositely with respect to the other two helical strips.

5. An endoscope according to claim 1, wherein one of said two tubes is formed as a braided structure, and the other of said two tubes comprises three helically wound strips arranged one over another, with an intermediate one of said three helical strips being wound oppositely with respect to the two other helical strips.

6. An endoscope according to claim 1, wherein one of said two tubes is formed as a braided structure, and the other tube comprises a single helically wound strip.

7. An endoscope according to claim 1, wherein one of said tubes comprises three helically wound strips arranged one over another, with an intermediate one of said helical strips being wound oppositely with respect to the other two helical strips, and the other tube comprises a single helically wound strip.

8. An endoscope according to claim 1, wherein at least one of said tubes is made of a metal material.

* * * * *